United States Patent
Walter et al.

(10) Patent No.: US 10,264,791 B2
(45) Date of Patent: Apr. 23, 2019

(54) ODOR-REDUCED PYRETHROID-ORGANOTHIOPHOSPHATE FORMULATIONS

(71) Applicant: FMC Corporation, Philadelphia, PA (US)

(72) Inventors: James Walter, Furlong, PA (US); Guozhi Wang, Oakland Gardens, NY (US); Kumar Vankayala, Bangalore (IN); Elizabeth E. Wolff, Fords, NJ (US)

(73) Assignee: FMC Corporation, Philadelphia, PA (US)

( * ) Notice: Subject to any disclaimer, the term of this patent is extended or adjusted under 35 U.S.C. 154(b) by 388 days.

(21) Appl. No.: 14/661,538

(22) Filed: Mar. 18, 2015

(65) Prior Publication Data

US 2015/0264934 A1 Sep. 24, 2015

(30) Foreign Application Priority Data

Mar. 20, 2014 (IN) .............................. 357/KOL/2014

(51) Int. Cl.
*A01N 57/28* (2006.01)
*A01N 53/00* (2006.01)
*A01N 25/08* (2006.01)
*A01N 25/12* (2006.01)

(52) U.S. Cl.
CPC ............ *A01N 57/28* (2013.01); *A01N 25/08* (2013.01); *A01N 25/12* (2013.01); *A01N 53/00* (2013.01)

(58) Field of Classification Search
None
See application file for complete search history.

(56) References Cited

U.S. PATENT DOCUMENTS

| 4,065,558 A | 12/1977 | Gordon |
| 4,948,787 A | 8/1990 | Chen et al. |
| 5,075,058 A | 12/1991 | Chan et al. |
| 5,100,667 A | 3/1992 | Chan et al. |
| 5,369,100 A | 11/1994 | Cummings |
| 2002/0115565 A1 | 8/2002 | Asrar et al. |
| 2003/0153484 A1 | 8/2003 | Gaytan |
| 2007/0014825 A1 | 1/2007 | Chan |
| 2009/0098016 A1 | 4/2009 | Koper et al. |
| 2012/0207806 A1* | 8/2012 | LoPesio ................. A01N 65/36 424/409 |

FOREIGN PATENT DOCUMENTS

| BR | PI0604545 A | 6/2008 |
| CH | 647132 A5 | 1/1985 |
| JP | H0721807 A | 1/1995 |

OTHER PUBLICATIONS

Singh, Amit et al. "Copper Coated Silica Nanoparticles for Odor Removal" Langmuir vol. 26, No. 20, Sep. 14, 2010, pp. 15837-15844, XP002739110.

Sattler, Melanie L. et al., "Removal of Carbonyl Sulfide Using Activated Carbon", Journal of the Air & Waste Management Association, vol. 56, 2006, pp. 219-224, XP55186961.

* cited by examiner

*Primary Examiner* — Alton N Pryor

(57) ABSTRACT

Microparticles comprising (a) a water-soluble solid organothiophosphate, (b) one or more odor-absorbing components, and (c) one or more odor-masking components are disclosed, as well as a method of making the microparticles, and odor-reduced insecticidal formulations comprising the microparticles. The microparticles and formulations can also contain other crop protection agents. Odor-reduced insecticidal formulations comprising (a) a pyrethroid, (b) an organothiophosphate, (c) one or more odor-absorbing components, and (d) one or more odor-masking components are also disclosed. Additionally disclosed is a method of reducing the odor of an organothiophosphate-containing formulation by incorporating one or more odor-absorbing components and one or more odor-masking components.

16 Claims, No Drawings

ODOR-REDUCED PYRETHROID-ORGANOTHIOPHOSPHATE FORMULATIONS

CROSS-REFERENCE TO RELATED APPLICATIONS

This application claims the benefit of priority of Indian Application No. 357/KOL/2014 filed on Mar. 20, 2014, the entire disclosure of which is incorporated herein by reference.

FIELD OF THE INVENTION

The present invention relates to the field of agrochemical compositions and formulations. In particular, the invention provides an insecticidal formulation comprising an organothiophosphate, for example acephate, which reduces or eliminates the negative odors normally associated with compositions containing organothiophosphate insecticides, and in the fields or plots treated therewith.

BACKGROUND OF THE INVENTION

It is important to treat crop plants and turf (such as golf course and grassy public park areas) with pesticides and/or other crop protection agents in order to control pest-induced damage to the crops or turf. For grower and/or public acceptance, the treatments ideally should leave no negative odor, or at most only a mild odor which is not considered to be negative, unpleasant or repulsive to humans.

One of the most well-established classes of insecticides is the organophosphates, with organothiophosphates and organodithiophosphates making up a significant subclass. For the purposes of the present invention the term "organothiophosphate" is meant to also include organodithiophosphates. The latter compounds are highly active, relatively safe and relatively inexpensive, providing an economic means of controlling insect pests. One of the most commercially important compounds in this class is acephate. Acephate, like other organothiophosphates, can leave an unpleasant, objectionable odor in the treated field. This negative odor can introduce restrictions on the times when the composition can be applied in areas frequented by members of the public. Such negative odors can also reduce grower acceptance of the product.

Previous attempts to produce odor-reduced formulations of organothiophosphates have focused on the addition of odor-masking agents, such as perfumes and volatile essential oils. Thus, acephate has been formulated with odor-masking agents to provide compositions in which the objectionable odors from the active ingredient have been masked at least to some degree (see U.S. Pat. No. 7,407,927, the entire contents of which are incorporated herein by reference).

There continues to be a need for more effective odor control in the formulations of organothiophosphates as well as combinations of organothiophosphates with other crop protection agents. Effective odor control also must not compromise the efficacy of the active ingredient(s), or the storage stability of the composition. The present invention is directed to meeting this need.

SUMMARY OF THE INVENTION

The present invention is directed to an insecticidal composition, particularly a solid formulation, comprising an organothiophosphate in which the negative odor is effectively controlled, with the formulation being stable over time. Effective control in the context of odor control means that the odor of the formulation is not negative to a human nose; that is, the objectionable odor is eliminated or is reduced so that the odor is acceptable, i.e. not unpleasant or repulsive. The formulation is preferably a solid formulation, including without limitation, dusts, wettable powders and granules of various sorts, including, for example water dispersible granules. In one embodiment the composition comprises an organothiophosphate; in another embodiment the composition comprises both an organothiophosphate and a pyrethroid. In one embodiment, the pyrethroid can be melted without decomposition. In one specific embodiment the organothiophosphate is acephate. In one embodiment, the pyrethroid is selected from the group consisting of bifenthrin, zeta-cypermethrin, permethrin, lambda-cyhalothrin, and tefluthrin. In another specific embodiment the pyrethroid is bifenthrin.

One aspect of the invention is directed to a microparticle that is composed of (a) a water-soluble solid organothiophosphate insecticide, (b) one or more odor-absorbing components, and (c) one or more odor-masking components. A second aspect of the invention is directed to a microparticle that contains (a) a pyrethroid, (b) a water-soluble solid organothiophosphate insecticide, (c) one or more odor-absorbing components, and (d) one or more odor-masking components. One embodiment of the latter is directed to a microparticle that contains at least (a) bifenthrin, (b) acephate, (c) one or more odor-absorbing components, and (d) one or more odor-masking components. The microparticle can further contain one or more components selected from the group consisting of solid carriers, surfactants, wetting agents, dispersants, anticaking agents, pH-regulating agents, preservatives, biocides and antifoaming agents. In one embodiment of the invention the odor-absorbing components of the microparticle are selected from the group consisting of charcoal, an aklanolamine compound and mixtures of two or more thereof. Preferably at least one odor-absorbing component is charcoal. In one embodiment the alkanolamine compound is triethanolamine. In a preferred embodiment, both charcoal and triethanolamine are present as odor-absorbing components. In one embodiment, the microparticle contains odor-masking components selected from the group consisting of perfumes, pleasant-smelling oils, essential oils, terpenes, esters and aldehydes.

In another aspect of the invention, an odor-resistant formulation comprises a plurality of microparticles, wherein such microparticles consist of at least one population of microparticles having an effective particle size ("D90") of less than about 250 microns; in another embodiment D90 is less than about 50 microns. In another embodiment, each microparticle in the above mentioned population of microparticles is composed of (a) a water-soluble solid organothiophosphate insecticide, (b) one or more odor-absorbing components, and (c) one or more odor-masking components. In a more preferred embodiment, the microparticle contains (a) a pyrethroid, (b) a water-soluble solid organothiophosphate insecticide, (c) one or more odor-absorbing components, and (d) one or more odor-masking components. In the most preferred embodiment each microparticle contains at least (a) bifenthrin, (b) acephate, (c) one or more odor-absorbing components, and (d) one or more odor-masking components.

In a specific embodiment the microparticle population has a particle size defined by D90 of between about 1 and about 250 microns.

In one embodiment, the ratio of bifenthrin:acephate in the microparticle is about 1:9. In another embodiment, the range can vary between 1:9 to 5:5.

Another aspect of the invention is directed to a reduced-odor formulation comprising the above-described microparticles, wherein the odor-absorbing and odor-masking components are present in amounts effective to reduce or eliminate objectionable odors.

A related aspect of the invention is directed to a reduced-odor formulation comprising (a) an organothiophosphate insecticide, (b) one or more odor-absorbing components, and (c) one or more odor-masking components, where components (b) and (c) are present in amounts effective to reduce or eliminate objectionable odors. A second aspect is directed to a reduced-odor formulation comprising (a) a pyrethroid, (b) an organothiophosphate insecticide, (c) one or more odor-absorbing components, and (d) one or more odor-masking components, where components (c) and (d) are present in amounts effective to reduce or eliminate objectionable odors. One embodiment of the latter is directed to a reduced-odor formulation comprising (a) bifenthrin, (b) acephate, (c) one or more odor-absorbing components, and (d) one or more odor-masking components, where components (c) and (d) are present in amounts effective to reduce or eliminate objectionable odors.

In one embodiment of the invention, the odor-absorbing components in total are present in about 0.1% to about 10% by weight of the total formulation. In another embodiment the odor-masking components in total are present in about 0.01% to about 10% by weight of the total formulation. In one embodiment the pyrethroid, e.g. bifenthrin, is coated or absorbed on a solid carrier, which can be selected from the group consisting of a silica, a hydrated aluminum-magnesium silicate. mommorillonite and attapulgite. Preferably, the solid carrier is amorphous precipitated silica.

In one embodiment the odor-absorbing components are selected from the group consisting of charcoal, an alkanolamine compound and mixtures of two or more thereof. Preferably, at least one odor-absorbing component is charcoal. In another preferred embodiment the alkanolamine compound is triethanolamine. More preferably, both charcoal and triethanolamine are present as odor-absorbing components.

In another embodiment the odor-masking components are selected from the group consisting of perfumes, pleasant-smelling oils, essential oils, terpenes, esters and aldehydes. Preferably, the odor-masking components are selected from the group consisting of lemon oil, limonene, camphor, geraniol, rose oil, citronella oil and peppermint oil. In one embodiment the esters are selected from the group consisting of ethyl acetate, butyl acetate and amyl acetate. In another embodiment the aldehydes are selected from the group consisting of octanal and citronellal.

In a preferred embodiment of the invention, the formulation is a solid formulation, which can be selected from the group consisting of wettable powders and granules. A preferred granule is a water-dispersible granule.

Yet another aspect of the invention is directed to a method of reducing the odor of an organothiophosphate insecticide formulation, comprising incorporating odor-reducing amounts of (a) one or more odor-absorbing components, and (b) one or more odor-masking components. The odor-absorbing and odor-masking components are present in combination in amounts that reduce or eliminate negative odors. Another aspect is directed to a pyrethroid-organothiophosphate formulation, comprising incorporating odor-reducing amounts of (a) one or more odor-absorbing components, and (b) one or more odor-masking components. The odor-absorbing and odor-masking components are present in combination in amounts that reduce or eliminate negative odors. One embodiment of the latter is directed to a bifenthrin-acephate formulation, comprising incorporating odor-reducing amounts of (a) one or more odor-absorbing components, and (b) one or more odor-masking components. In one embodiment the odor-absorbing components in total are present in about 0.1% to about 10% by weight of the total formulation. In another embodiment the odor-masking components in total are present in about 0.01% to about 10% by weight of the total formulation. Still another aspect of the invention is directed to a method of making odor-reduced microparticles, comprising the steps of (a) providing a pyrethroid coated or absorbed on a carrier, preferably a solid carrier; (b) providing a mixture of one or more odor-absorbing agents, one or more odor-masking agents and one or more surfactants; (c) blending the pyrethroid-on-carrier, a water-soluble organothiophosphate insecticide and the anti-odor mixture together with one or more wetting agents and one or more dispersants to form a blended mixture; (d) blending with sodium sulfate and/or ammonium sulfate, and (e) milling the blended mixture, to produce an odor-reduced wettable powder. One embodiment is directed to a method of making odor-reduced microparticles, comprising the steps of (a) providing bifenthrin coated or absorbed on a carrier; (b) providing a mixture of one or more odor-absorbing agents, one or more odor-masking agents and one or more surfactants; (c) blending the bifenthrin-on-carrier, acephate and the anti-odor mixture together with one or more wetting agents and one or more dispersants to form a blended mixture; and (d) milling the blended mixture, optionally together with sodium sulfate and/or ammonium sulfate, to produce an odor-reduced wettable powder. In one embodiment, the wettable powder contains about 5% bifenthrin and about 45% acephate. In another embodiment, the pyrethroid-on-carrier has a particle size D90 of less than about 20 microns.

DETAILED DESCRIPTION OF PREFERRED EMBODIMENTS

The odor-reduced formulations of the present invention provide for both the masking of offensive odor, and the prevention of the emission of toxic, malodorous volatile substances into the air by absorption of these volatile components. The use of an odor-masking agent alone can only mask the negative odor of an organothiophosphate insecticide such as acephate and/or its degradation products, and does nothing to prevent the emission of malodorous volatiles into the air. Thus the present formulation reduces the offensive odor of an organothiophosphate-containing composition by combining both absorption and masking of the malodorous volatiles. Absorption of malodorous compounds is accomplished using one or more odor-absorbing components, including without limitation, charcoal, alkanolamines and mixtures thereof. At the same time any remaining offensive odors are masked with one or more odor-masking components including, without limitation, perfumes, volatile oils with pleasant smells such as essential oils, volatile terpenes, volatile esters such as ethyl acetate, butyl acetate, and amyl acetate and volatile aldehydes such as octanal and citronellal. Thus, the formulations of the invention possess both odor-masking and odor-absorbing properties, thereby providing insecticidal compositions that are acceptable to growers, handlers and the public. As used herein and unless otherwise indicated, the term "crop protection agent" refers to a molecule or combination of molecules which express biological activity as a pesticide, arthropodicide, insecticide, acaricide, nematocide, fungicide, selective herbicide, plant growth regulator or a combination of two or more of these biological activities. As used in this specification and unless otherwise indicated, the term "insecticide" refers to a molecule or combination of molecules that repels, retards, or kills insects, and can be used for crop protection or turf protection. The term "ambient temperature" as utilized herein shall mean any suitable temperature found in a laboratory or other working environment, including a field environment, and is generally not below about 15° C. nor above about 30° C.

The term "odor-reduced" or "odor-controlled" means that the odor of the formulation is not negative to a human nose; that is, any objectionable odor is eliminated or is reduced so that the odor of the composition, and the odor of the area to which it is applied are acceptable, i.e. not unpleasant or repulsive. Beyond the human nose, any known methodology in odor detection is applicable to the quantification of the amount of odor improvement, as indicated by the reduction or control of negative odors, obtained with the inventive formulations. Preferably at least a 10% reduction in negative odor is achieved with the present formulations, compared to those lacking the combination of both odor-absorbing and odor-masking components. More preferably, at least a 20% reduction in negative odor is achieved; still more preferably at least a 30% reduction in negative odor is achieved. In certain preferred embodiments at least a 40% reduction, at least a 50% reduction, at least a 60% reduction, at least a 70% reduction, or at least an 80% reduction of negative odor is achieved. In the most preferred embodiments, at least a 90% reduction, at least a 95% reduction, or about a 99 to 100% reduction in negative odor are achieved. In certain embodiments, the amount of odor improvement as detailed above can be determined by the application of grass chromatography with mass spectrometry (GC-MS), since this technology is capable of the efficient separation required for analysis and quantification of complex mixtures of volatile organic compounds.

The term "solid formulation" includes without limitation, dusts, wettable powders and granular formulations. An example of the latter is a water-dispersible granule.

The modifier "about" is used herein to indicate that certain preferred operating ranges, such as ranges for molar ratios for reactants, material amounts, and temperature, are not fixedly determined. The meaning will often be apparent to one of ordinary skill. For example, a recitation of a temperature range of about 120° C. to about 135° C. in reference to, for example, an organic chemical reaction would be interpreted to include other like temperatures that can be expected to favor a useful reaction rate for the reaction, such as 105° C. or 150° C. Where guidance from the experience of those of ordinary skill is lacking, guidance from the context is lacking, and where a more specific rule is not recited below, the "about" range shall be not more than 5% of the absolute value of an end point or 5% of the range recited, whichever is less.

Unless otherwise noted, the percentages used in the present application are percentages by weight, based on the total composition.

As used herein, "D50" refers to the particle size below which 50% of the particles in the population fall. Accordingly, "a D50 particle size of less than about 250 microns in diameter" means that at least 50% of the microparticles of the formulation are less than about 250 microns in diameter. Similarly, as used herein "D90" refers to the particle size below which 90% of the particles in the population fall. Accordingly, "a D90 particle size of less than about 250 microns in diameter" means that at least 90% of the microparticles of the formulation are about 250 microns or less in diameter.

The hydrated aluminum-magnesium silicate is preferably selected from montmorillonite clay, continental clay, kaolin clay and attapulgite clay.

One aspect of the invention is directed to a microparticle comprising (a) a water-soluble solid organothiophosphate insecticide, (b) one or more odor-absorbing components, and (c) one or more odor-masking components. Optionally, the microparticle can also comprise another crop protection agent, preferably another insecticide, acaricide, nematocide, arthropodicide or the like. A second aspect of the invention is directed to a microparticle comprising (a) a pyrethroid, (b) a water-soluble solid organothiophosphate insecticide, (c) one or more odor-absorbing components, and (d) one or more odor-masking components. One embodiment of the latter is directed to a microparticle comprising (a) bifenthrin, (b) acephate, (c) one or more odor-absorbing components, and (d) one or more odor-masking components. The microparticle can further comprise one or more components selected from the group consisting of solid carriers, surfactants, wetting agents, dispersants, anticaking agents, pH-regulating agents, preservatives, biocides and antifoaming agents. In one embodiment of the invention the odor-absorbing components of the microparticle are selected from the group consisting of charcoal, an aklanolamine compound and mixtures of two or more thereof. Preferably at least one odor-absorbing component is charcoal. The alkanolamine typically will contain from 2 to about 6 carbon atoms. In one embodiment the alkanolamine compound is selected from monoethanolamine; diethanolamine; triethanolamine; linear or iso-, mono-, di- or tri-propanolamines, salts thereof and derivatives thereof. Preferably the alkanolamine compound is triethanolamine. In a preferred embodiment, both charcoal and triethanolamine are present as odor-absorbing components. In one embodiment, the microparticle contains odor-masking components selected from the group consisting of perfumes, pleasant-smelling oils, essential oils, terpenes, esters and aldehydes.

The pyrethroid is preferably one which can be melted without decomposition, with melting being a precursor to spraying onto a solid support or carrier, such as silica. Preferably, the pyrethroid is a low-melting pyrethroid. In one embodiment the pyrethroid has a melting point of less than about 100° C.; in another embodiment the pyrethroid has a melting point of less than about 50° C.; in another embodiment the pyrethroid has a melting point of less than about 40° C.; in yet another embodiment, the pyrethroid has a melting point of less than about 35° C. In one embodiment, the pyrethroid is selected from the group consisting of bifenthrin, zeta-cypermethrin, permethrin, lambda-cyhalothrin, and tefluthrin.

In another aspect of the invention, an odor-resistant formulation comprises a plurality of microparticles, wherein such microparticles consist of at least one population of microparticles having a D90 of less than about 400 microns; in another embodiment the D90 is less than about 250 microns; in another embodiment D90 is less than about 50 microns; and in yet another embodiment D90 is less than about 20 microns.

In another aspect of the invention, an odor-resistant formulation comprises a plurality of microparticles, wherein such microparticles consist of at least one population of microparticles having a D50 of less than about 250 microns;

in another embodiment the D50 is less than about 100 microns; in yet another embodiment D50 is less than about 50 microns; and in a preferred embodiment D50 is less than about 20 microns.

In another embodiment, each microparticle in the above mentioned population of microparticles is composed of (a) a water-soluble solid organothiophosphate insecticide, (b) one or more odor-absorbing components, and (c) one or more odor-masking components. In a more preferred embodiment, the microparticle contains (a) a pyrethroid, (b) a water-soluble solid organothiophosphate insecticide, (c) one or more odor-absorbing components, and (d) one or more odor-masking components. For the purposes of the present invention, "solid" means that the compound exists in solid form at ambient temperature, as defined above. In one embodiment, the pyrethroid is selected from the group consisting of bifenthrin, zeta-cypermethrin, permethrin, lambda-cyhalothrin, and tefluthrin. In the most preferred embodiment each microparticle contains at least (a) bifenthrin, (b) acephate, (c) one or more odor-absorbing components, and (d) one or more odor-masking components.

In specific embodiments the microparticle population of the pyrethroid coated or absorbed on a carrier ("pyrethroid-on-carrier") has a particle size defined by D90 of between about 1 and about 50 microns and more preferably between about 10 to about 20 microns. In one embodiment the pyrethroid-on-carrier microparticles have a D90 of less than about 20 microns. In another embodiment the microparticle population of the organothiophosphate, preferably acephate, and any inorganic salts of the formulation, such as sodium sulfate and/or ammonium sulfate, have a particle size defined by D90 of between about 1 and about 250 microns, preferably about 120 to about 250 microns. In another embodiment the D90 of the organothiophosphate and inorganic salts is less than about 250 microns.

In one embodiment, the ratio of pyrethroid:organothiophosphate in the microparticle is about 1:100 to about 100:1. In at least one embodiment, the ratio is about 1:25 to about 25:1. In a preferred embodiment the ratio is about 1:9 to about 9:1. In one preferred embodiment the bifenthrin:acephate ratio is about 1:9. The ratio can be adjusted based on the particular pests to be controlled and the particular crop or turf, as well as the chemical and physical stabilities of the specific formulations as influenced by other formulation components. Another aspect of the invention is directed to a reduced-odor formulation comprising the above-described microparticles, wherein the odor-absorbing and odor-masking components are present in amounts effective to reduce or eliminate objectionable odors.

A related aspect of the invention is directed to a reduced-odor formulation comprising (a) an organothiophosphate insecticide, (b) one or more odor-absorbing components, and (c) one or more odor-masking components, where components (b) and (c) are present in amounts effective to reduce or eliminate objectionable odors. Optionally, the formulation can also comprise another crop protection agent, preferably another insecticide, acaricide, nematocide, arthropodicide or the like. A specific aspect is directed to a reduced-odor formulation comprising (a) a pyrethroid, (b) an organothiophosphate insecticide, (c) one or more odor-absorbing components, and (d) one or more odor-masking components, where components (c) and (d) are present in amounts effective to reduce or eliminate objectionable odors. In one embodiment, the pyrethroid is selected from the group consisting of bifenthrin, zeta-cypermethrin, permethrin, lambda-cyhalothrin, and tefluthrin. One embodiment of the latter is directed to a reduced-odor formulation comprising (a) bifenthrin, (b) acephate, (c) one or more odor-absorbing components, and (d) one or more odor-masking components, where components (c) and (d) are present in amounts effective to reduce or eliminate objectionable odors. The amounts of the odor-absorbing and odor-masking components required for odor reduction, and their relative ratio, depend on the concentration of the organothiophosphate in the composition, as well as its purity, and can readily be determined by one skilled in the art. In one embodiment of the invention, the odor-absorbing components are present in a combined total of about 0.1% to about 10% by weight based on the total formulation. In another embodiment the odor-masking components are present in a combined total of about 0.01% to about 10% by weight based on the total formulation. In one embodiment of a solid formulation, bifenthrin is coated or absorbed on a solid carrier, which can be selected from the group consisting of a silica, a hydrated aluminum-magnesium silicate, montmorillonite and attapulgite. In a preferred formulation the solid carrier is amorphous precipitated silica.

In one embodiment the odor-absorbing components are selected from the group consisting of charcoal, an alkanolamine compound and mixtures of two or more thereof. The alkanolamine typically will contain from 2 to about 6 carbon atoms.

The charcoal is preferably activated charcoal (also known as activated carbon). The ethanolamine compound can be selected from the group consisting of monoethanolamine, diethanolamine, triethanolamine, salts thereof, derivatives thereof and mixtures of two or more thereof. Salts of alkanolamines include, without limitation, hydrohalides, such as hydrochloride or hydrobromide, salts of other inorganic acids such as sulfuric acid, phosphoric acid and nitric acid, and salts of organic acids such as acetic acid. Preferably, at least one odor-absorbing component is charcoal. In another preferred embodiment the alkanolamine compound is triethanolamine. More preferably, both charcoal and triethanolamine, either as a free base or a salt, are present as odor-absorbing components.

In another embodiment the odor-masking components are selected from the group consisting of perfumes, pleasant-smelling oils, essential oils, terpenes, esters and aldehydes. Preferably, the odor-masking components are selected from the group consisting of lemon oil, limonene, camphor, geraniol, rose oil, citronella oil and peppermint oil. In one embodiment the esters are selected from the group consisting of lower alkyl acetates, where lower alkyl is branched or unbranched $C_1$ to $C_6$ alkyl, such as ethyl acetate, butyl acetate or amyl acetate. In another embodiment the aldehydes are selected from volatile aldehydes, including without limitation, the group consisting of branched, unbranched, cyclic and bicyclic aldehydes having from about 5 to about 24 carbon atoms. Preferably, the aldehydes are selected from octanal and citronellal.

In a preferred embodiment of the invention, the formulation is a solid formulation, which can be selected from the group consisting of dusts, wettable powders and granules. In one preferred embodiment the formulation is a wettable powder. In another preferred embodiment the formulation is a water-dispersible granule.

Yet another aspect of the invention is directed to a method of reducing the odor of an organothiophosphate insecticide formulation, comprising incorporating odor-reducing amounts of (a) one or more odor-absorbing components, and (b) one or more odor-masking components. Optionally, the method can also comprise another crop protection agent in the insecticide formulation, preferably another insecticide, acaricide, nematocide, arthropodicide or the like. A specific aspect is directed to a pyrethroid-organothiophosphate formulation, comprising incorporating odor-reducing amounts of (a) one or more odor-absorbing components, and (b) one or more odor-masking components. One embodiment of the latter is directed to a bifenthrin-acephate formulation, comprising incorporating odor-reducing amounts of (a) one or more odor-absorbing components, and (b) one or more odor-masking components. The amounts of (a) and (b) required for odor reduction, and their relative ratio, depend on the concentration of the organothiophosphate in the composition, as well as its purity, and can readily be determined by one skilled in the art. The odor-absorbing and odor-masking components are as described above. In one embodiment the odor-absorbing components are present in a combined total of about 0.1% to about 10% by weight based on the total formulation. In another embodiment the odor-masking components are present in a combined total of about 0.01% to about 10% by weight based on the total formulation.

Still another aspect of the invention is directed to a method of making odor-reduced microparticles, comprising the steps of (a) providing a pyrethroid coated or absorbed on a carrier; (b) providing a mixture of one or more odor-absorbing agents, one or more odor-masking agents and one or more surfactants; (c) blending the pyrethroid-on-carrier, a water-soluble organothiophosphate insecticide and the anti-odor mixture together with one or more wetting agents and one or more dispersants to form a blended mixture; and (d) blending with sodium sulfate and/or ammonium sulfate, (e) milling the blended mixture, to produce an odor-reduced wettable powder. In one embodiment, the pyrethroid is selected from the group consisting of bifenthrin, zeta-cypermethrin, permethrin, lambda-cyhalothrin, and tefluthrin. One embodiment of the latter is directed to a method of making odor-reduced microparticles, comprising the steps of (a) providing bifenthrin coated or absorbed on a carrier; (b) providing a mixture of one or more odor-absorbing agents, one or more odor-masking agents and one or more surfactants; (c) blending the bifenthrin-on-carrier, acephate and the anti-odor mixture together with one or more wetting agents and one or more dispersants to form a blended mixture; and (d) milling the blended mixture, optionally together with sodium sulfate and/or ammonium sulfate, to produce an odor-reduced wettable powder. In one embodiment, the wettable powder contains about 2% to about 10% of bifenthrin and about 25% to about 60% of acephate, preferably about 3% to about 6% of bifenthrin and about 30% to about 50% of acephate. In one embodiment, the wettable powder contains about 3% to about 9% by weight of bifenthrin. In one embodiment, the wettable powder contains about 4% to about 8% by weight of bifenthrin. In one embodiment, the wettable powder contains about 5% to about 7% by weight of bifenthrin. In one embodiment, the wettable powder contains 30% to about 55% of acephate. In one embodiment, the wettable powder contains 35% to about 50% of acephate. In one embodiment, the wettable powder contains 40% to about 50% of acephate. One embodiment of the method provides a wettable powder containing about 5% bifenthrin and about 45% acephate.

The compositions and methods of the present invention are further illustrated by the following examples. These examples serve merely to illustrate particular embodiments of the invention and are not intended to limit the scope of the invention in any way. Further modifications encompassed by the disclosed invention will be apparent to those skilled in the art. All such modifications are deemed to be within the scope of the invention as defined in the present specification and claims.

EXAMPLES

Example 1

Odor-Controlled Wettable Powder Formulation Containing an Organothiophosphate Insecticide Step A A 45%/55% weight to weight mixture of bifenthrin technical (98% purity) absorbed on amorphous precipitated silica was prepared by melting bifenthrin technical at about 85° C. to 90° C. The melted bifenthrin was sprayed onto preheated (about 75° C.) amorphous precipitated silica (Sipernat® 50S, Evonik Industries) in a plow mixer in which the plow blades and chopper blades were on. After the addition of bifenthrin was complete, mixing was continued for an additional 15 minutes. A few seed crystals of bifenthrin technical were distributed into the mixer and the mixture was transferred into a ribbon blender and blended for an additional 15 minutes.

Step B

A mixture of 2.18 grams of activated charcoal and 0.2 gram of a dialkylnaphthalene sulphonate sodium salt (SUPRAGIL® WP, Rhodia) was placed into a pulverizing blender. The blender was started and a mixture of 1.0 gram of amyl acetate, 0.2 gram of triethanolamine (TEA) and 0.3 gram of octanal was added drop wise. The blender was stopped and 10.84 grams of the bifenthrin mixture prepared in Step A, 46.0 grams of acephate (98% purity), 0.1 gram of a linear alkylbenzene sulfonate (STEPWET® DF-90, Stepan Company), 0.3 gram of kraft lignosulfonate (POLYFON® H, MeadWestvaco Corporation) and 0.3 gram of a highly sulfonated kraft lignin (REAX® 88B, MeadWestvaco Corporation) were added and the blender was turned on at high speed. After about one minute the blender was stopped and the resultant mixture was transferred into a hammer mill fitted with a 200 micron screen. Sodium sulfate (13.8 grams) and 25.0 grams of ammonium sulfate was also added to the hammer mill. The mixture was milled to produce a wettable powder containing 4.4% bifenthrin and 46.0% acephate, having a particle size (D90) of 19.06 microns.

There was no odor of acephate at the time of preparation. The wettable powder formulation was labeled Formulation 1-1 and placed into a glass jar and sealed. After 9 months at room temperature the jar was unsealed and a very slight, but acceptable, i.e. not unpleasant or repulsive, odor of acephate was detected.

Additional formulations were prepared in the same manner as Example 1 Step B and are summarized in Table 1 below. The table also summarizes odor control data from these formulations.

TABLE 1

Low Odor Formulations Containing Acephate and Bifenthrin

| Formulation Ingredient | Formulation Number-Ingredient Amount (grams) | | | | | | |
|---|---|---|---|---|---|---|---|
| | 1-2 | 1-3 | 1-4 | 1-5 | 1-6 | 1-7 | 1-8 |
| Bifenthrin Step A | 10.8 | 10.8 | 11.6 | 11.6 | 11.6 | 11.6 | 11.6 |
| STEPWET ® DF-90 | 0.2 | 0.1 | 0.2 | 0.1 | 0.1 | 0.1 | 0.1 |
| POLYFON ® H | 0.3 | 0.3 | 0.3 | 0.3 | 0.3 | 0.3 | 0.3 |
| REAX ® 88B | 0.2 | 0.3 | 0.3 | 0.3 | 0.3 | 0.3 | 0.3 |
| Acephate | 46.0 | 16.2 | 46.1 | 46.2 | 46.0 | 46.0 | 46.0 |
| Sodium sulfate | 13.8 | 13.8 | 13.0 | 13.0 | 13.0 | 13.0 | 13.0 |
| Ammonium sulfate | 25.0 | 25.0 | 25.2 | 25.0 | 25.0 | 25.0 | 25.0 |
| SUPRAGIL ® WP | 0.2 | 0.21 | 0.2 | 0.2 | 0.2 | 0.2 | 0.2 |
| Charcoal | 2.0 | 2.1 | 2.0 | 2.0 | 2.0 | 2.0 | 2.0 |
| Triethanolamine | 0.2 | 2.2 | 0.2 | 0.2 | 0.2 | 0.2 | 0.2 |
| Octanal | 0.5 | 0.3 | 0.5 | 0.5 | 0.5 | 0.5 | 0.5 |
| Odor-masking agent | lemon oil 0.8 | d-limonene 1.1 | n-butyl acetate 0.8 | camphor 0.8 | geraniol 0.8 | citronella oil 0.8 | Peppermint oil 0.8 |
| Initial odor | No Odor | No Odor | No Odor | No Odor | No Odor | No Odor | No Odor |
| Odor after 6 months @ room temperature | ND | ND | ND | Slight Odor | No Odor; Slight geraniol smell | No Odor; Slight citronella smell | No Odor; Slight peppermint smell |
| Odor after 9 months @ room temperature | Slight Odor | No Odor | Slight Odor | | | | |

ND = not determined
No Odor = no negative odor of acephate or its decomposition products present; Slight Odor = odor present, but acceptable, i.e. not unpleasant or repulsive. Odor was determined by gently wafting the volatiles from the storage container and smelling/sniffing the volatiles by a human volunteer.

Comparative Example A

Charcoal Only. Wettable Powder Formulation Containing an Organothiophosphate Insecticide Step A A mixture of 100.16 grams of bifenthrin mixture as prepared in Example 1 Step A, 2.01 grams of STEPWET® D90, 3.03 grams of POLYFON® H and 2.07 grams of REAX® 88B was air milled until a particle size of less than 6 microns was achieved.

Step B

A mixture of 46.0 grams of acephate, 41.5 grams of sodium sulfate and 1.0 gram of activated charcoal was Air milled until a particle size of about 6 microns was achieved. To this was added 11.5 grams of the bifenthrin mixture from Step A and mixed until homogenous. This composition was placed into a glass jar and sealed. After 9 months at room temperature the jar was opened and was found to have no odor control as a very strong smell of acephate was detected.

Comparative Example B

No Charcoal. Wettable Powder Formulation Containing an Organothiophosphate Insecticide Into a pulverizing blender was placed 10.90 grams of the bifenthrin mixture as prepared in Example 1, Step A. The blender was started and a mixture of 1.00 gram of ethyl acetate, 0.31 gram of triethanolamine (TEA) and 0.26 gram of octanal was added drop wise. 0.2 gram of a dialkylnaphthalene sulphonate sodium salt (SUPRAGIL® WP, Rhodia) was placed. The blender was stopped and 46.16 grams of acephate (98% purity), 0.22 gram of a linear alkylbenzene sulfonate (STEPWET® DF-90, Stepan Company), 0.36 gm of kraft lignosulfonate (POLYFON® H, MeadWestvaco Corporation), 0.21 gram of a highly sulfonated kraft lignin (REAX® 88B, MeadWestvaco Corporation), 26.00 grams of sodium sulfate and 25.0 grams of ammonium sulfate were added and the blender was turned on at high speed. After about one minute the blender was stopped and the resultant mixture was transferred into a hammer mill fitted with a 200 micron screen. The mixture was milled to produce a wettable powder containing 4.3% bifenthrin and 46.0% acephate, having a particle size (D90) of 16.49 microns. There was no odor of acephate at the time of preparation. This wettable powder formulation was placed into a glass jar and sealed. After 9 months at room temperature the jar was unsealed and a very noticeable and unpleasant odor of acephate was detected.

What is claimed is:

1. A microparticle comprising:
   (a) a pyrethroid;
   (b) a water-soluble solid organothiophosphate insecticide;
   (c) one or more odor-absorbing components; and
   (d) one or more odor-masking components.

2. The microparticle of claim 1, wherein said pyrethroid is selected from the group consisting of bifenthrin, zeta-cypermethrin, permethrin, lambda-cyhalothrin, and tefluthrin.

3. The microparticle of claim 1, where said organothiophosphate insecticide is acephate.

4. The microparticle of claim 1, wherein said odor-absorbing components are selected from the group consisting of charcoal, an alkanolamine compound and mixtures of two or more thereof.

5. The microparticle of claim 1, wherein said odor-masking components are selected from the group consisting of perfumes, pleasant-smelling oils, essential oils, terpenes, esters and aldehydes.

6. The microparticle of claim 1, wherein said pyrethroid is bifenthrin and said organothiophosphate insecticide is acephate, and the weight ratio of bifenthrin:acephate is about 1:9.

7. A reduced-odor formulation comprising the microparticle of claim 1, wherein said odor-absorbing and odor-masking components are present in amounts effective to reduce or eliminate objectionable odors.

8. A formulation comprising a microparticle of claim 1 wherein the formulation includes:
about 0.1% to about 10% by weight of the total formulation of the one or more odor-absorbing components; and
about 0.01% to about 10% by weight of the total formulation of the one or more odor-masking components; and wherein the odor-absorbing and odor-masking components are present in amounts effective to reduce or eliminate objectionable odors.

9. The formulation of claim 8, wherein said pyrethroid is selected from the group consisting of bifenthrin, zeta-cypermethrin, permethrin, lambda-cyhalothrin and tefluthrin.

10. The formulation of claim 8, where said organothiophosphate insecticide is acephate.

11. The formulation of claim 8, wherein said pyrethroid is absorbed on a solid carrier selected from the group consisting of a silica, a hydrated aluminum-magnesium silicate, montmorillonite and attapulgite.

12. The formulation of claim 11, wherein said pyrethroid is bifenthrin and said organothiophosphate insecticide is acephate.

13. The formulation of claim 8, wherein said odor-absorbing components are selected from the group consisting of charcoal, an alkanolamine compound and mixtures of two or more thereof.

14. The formulation of claim 8, wherein said odor-masking components are selected from the group consisting of lemon oil, limonene, camphor, geraniol, rose oil, citronella oil, peppermint oil, ethyl acetate, butyl acetate and amyl acetate, octanal and citronellal.

15. A method of reducing odor emanating from a pyrethroid-organothiophosphate formulation, comprising incorporating a microparticle of claim 1 comprising odor-reducing amounts of:
(a) about 0.1% to about 10% by weight of the total formulation of the one or more odor-absorbing components; and
(b) about 0.01% to about 10% by weight of the total formulation of the one or more odor-masking components.

16. The method of claim 15, wherein said organothiophosphate insecticide is acephate.

* * * * *